United States Patent [19]

Schmid et al.

[11] Patent Number: 4,967,017

[45] Date of Patent: Oct. 30, 1990

[54] ALCOHOL ETHOXYLATES OF REDUCED EO CONTENT OR RESIDUAL PO CONTENT

[75] Inventors: Karl Schmid, Mettmann; Alfred Meffert, Monheim; Klaus Friedrich, Duesseldorf; Michael Langen, Hilden; Klaus Herrmann, Monheim, all of Fed. Rep. of Germany

[73] Assignee: Henkel Kommanditgesellschaft auf Aktien, Duesseldorf-Holthausen, Fed. Rep. of Germany

[21] Appl. No.: 332,673

[22] Filed: Mar. 31, 1989

[30] Foreign Application Priority Data

Apr. 2, 1988 [DE] Fed. Rep. of Germany ....... 3811319

[51] Int. Cl.$^5$ ...................... C07C 41/03; C07C 37/68
[52] U.S. Cl. ..................... 568/621; 518/618; 518/608
[58] Field of Search ........................ 568/618, 621, 608

[56] References Cited

U.S. PATENT DOCUMENTS

| | | | |
|---|---|---|---|
| 2,355,823 | 8/1944 | Schlegal | 568/618 |
| 2,425,755 | 8/1947 | Roberts et al. | 568/618 |
| 2,448,664 | 9/1948 | Fife et al. | 568/618 |
| 4,129,718 | 12/1978 | Muzzio | 568/621 |
| 4,456,773 | 6/1984 | Fock | 568/618 |
| 4,507,475 | 3/1985 | Strackle et al. | 568/621 |

FOREIGN PATENT DOCUMENTS

| | | | |
|---|---|---|---|
| 1240062 | 5/1967 | Fed. Rep. of Germany | 568/618 |
| 3708813 | 9/1988 | Fed. Rep. of Germany | |
| 1228461 | 4/1971 | United Kingdom | 568/621 |

*Primary Examiner*—Howard T. Mars
*Attorney, Agent, or Firm*—Ernest G. Szoke; Wayne C. Jaeschke; Henry E. Millson, Jr.

[57] ABSTRACT

A process for the production of alcohol polyglycol ethers by reaction of an alcohol with ethylene oxide and/or propylene oxide wherein a basic alkali metal compound catalyst is employed in at least 0.5% by weight, expressed as sodium methylate, and based on the total weight of the reactants. The reaction mixture is neutralized in the presence of a filter aid.

15 Claims, No Drawings

ALCOHOL ETHOXYLATES OF REDUCED EO CONTENT OR RESIDUAL PO CONTENT

BACKGROUND OF THE INVENTION

1. Field of the Invention.

This invention relates to alcohol ethoxlates which have a low residual ethylene oxide or propylene oxide content.

2. Statement of Related Art.

Surface-active alkyl polyglycol ethers from the reaction of relatively long chain alcohols with ethylene oxide and/or propylene oxide have been known for decades. They are important representatives of the class of nonionic surfactants. Wetting or emulsifying auxiliaries of similar structure are obtained by ethoxylation of comparable components containing free hydroxyl groups while low-foam surfactants are obtained by addition of propylene oxide and, optionally, ethylene oxide onto such components. Partial derivatives of polyhydric alcohols with relatively long chain reactants are mentioned as examples. Typical examples are partial esters of such polyhydric alcohols with relatively long-chain carboxylic acids, for example with fatty acids of natural and/or synthetic origin. Starting materials of this type, for example corresponding glycerol partial esters or sorbitan partial esters, are also converted by ethoxylation/propoxylation into corresponding reaction products containing polyglycol ether groups which have wetting and/or emulsifying or low-foam properties and which are widely used in cosmetics, in the textile field, particularly in the washing of textiles, and/or generally in the home and in industry.

The ethoxylation or propoxylation of such alcohol functions is carried out at elevated temperature and pressure in the presence of acidic or basic catalysts. The use of basic compounds of the alkali metals is of particular significance in this regard in all those cases where the starting compounds to be ethoxylated show a substantially neutral reaction. Such basic catalysts include, primarily, sodium and/or potassium alkoxylates, such as sodium or potassium methylate or the corresponding ethylates. Other commonly used basic alkali metal catalysts are sodium and potassium hydroxide.

In addition to satisfying the reqirements which active surfactants in general have to meet, a certain characteristic of these auxiliaries has recently been receiving increasing attention in regard to the use of the above-mentioned nonionic surfactants in practice, namely their residual content of unreacted ethylene oxide. Thus, according to a recommendation of the Bundesgesundheitsamt der Bundesrepublik Deutschland (Federal Health Office of the Federal Republic of Germany), cf. Bundesgesundheitsblatt 29 (1986), pages 21, 22, the content of free EO in the nonionic surfactant should not exceed a limit of 1 ppm if the application envisaged for the compounds in question here involves close contact with the body. To establish residual EO contents as low as these, additional purification measures were necessary for the ethoxylation processes hitherto practised on an industrial scale using alkaline catalysts. Thus, according to Applicant's earlier German patent application P 37 08 813 (D 7844), the residual content of free EO in the ethoxylation product is reduced to the necessary levels by treatment with steam.

The same concerns apply to propoxylation where it is also desired to obtain propoxylates having the lowest possible residual contents of free PO.

DESCRIPTION OF THE INVENTION

Other than in the operating examples, or where otherwise indicated, all numbers expressing quantities of ingredients or reaction conditions used herein are to be understood as modified in all instances by the term "about".

An object of the present invention is to modify the known ethoxylation of alcoholic starting components of the above described type in the presence of basic catalysts, particularly basic alkali metal compounds, in such a way that ethoxylates or propoxylates which, in addition to the required technical specifications, are also distinguished by the required relatively low content of free EO and PO, are directly obtained as the primary reaction product.

It has surprisingly been found that reaction products of the required type can be obtained by carrying out the reaction with comparatively high concentrations of catalyst above those used at present in industrial processes. In addition, it is possible in accordance with the invention to obtain further important advantages for the reaction products produced in this way, as will be described in detail hereinafter. It is particularly important in this regard that the teaching according to the invention enables the residual content of free EO or PO to be reduced without the proven properties, more especially the wetting and/or emulsifying properties, of the particular reaction product being substantially affected.

In a first embodiment, thereofore, the present invention relates to a process for the production of alcohol polyglycol ethers by reaction of the alcohol components with ethylene oxide or propylene oxide at elevated temperatures in the presence of basic alkali metal compounds as catalysts. The basic alkali metal compounds, in order to reduce the residual content of free ethylene oxide to values below 1 ppm or to reduce the residual content of free propylene oxide to values below 5 ppm in the primary reaction product obtained, are used in a minimum concentration of at least 0.5% by weight, expressed as sodium methylate, and based on the total mixture of the alcohol component used and ethylene oxide or propylene oxide. Instead of sodium methylate, other known basic alkali metal catalysts, such as potassium methylate, sodium or potassium ethylate, sodium or potassium hydroxide, and other sodium or potassium alkoxylates, or mixtures of the foregoing can also be used in equivalent quantities.

In a preferred embodiment of the invention, the alkoxylation is carried out with a minimum concentration of 0.8% by weight of the basic catalyst, again expressed as sodium methylate as the catalytic compound and based on the sum total of reactants used. According to the invention, it is possible to reduce the residual EO content of the primary reaction product obtained to values of at most about 0.5 ppm, with the residual contents of free EO in the primary reaction product generally being below the detection limit applied at present of approximately 0 1 ppm. The corresponding residual contents of free PO are below 5 ppm.

The prior art has been concerned at length with the production of alkyl polyglycol ether reaction products using increased quantities of alkaline catalysts of the above type. In particular, it is known that reaction products of narrow homolog distribution are obtained by the use of increased quantities of catalyst.

Although, in the interests of simplicity, the alkoxylate reaction products formed in the alcohol alkoxylation are stoichiometrically formulated, for example as $C_{12-14}$ fatty alcohol +9 EO, a mixture of homologous alkoxylates of reaction products having comparatively low to comparatively high degrees of alkoxylation is in reality present as the reaction product. The particular homolog distribution follows laws derived from the structure of the alcohol used and the alkoxylation conditions. The quantity and type of catalyst used play an important role in this regard. Important applicational properties, such as wetting power, washing power, cleaning power, emulsifying power, foam-inhibiting effect and the like, are determined by the particular homolog distribution curve of the reaction products. The commercial products available at present on the market show an optimized performance level in this regard which should be regarded as the basic practical standard for any modifications in the homolog distribution of corresponding reaction products and, as far as possible, should not be changed. Varying statements on the effect of using increased concentrations of catalyst on applicational properties, including in particular wetting or emulsifying power, can be found in the relevant prior art. In some cases, unwanted changes are postulated whereas, according to other statements, there are said to be no serious changes in this regard.

An object of the present invention is provide reaction mixtures of the described type which fully correspond in their applicational properties to the standard now demanded in practice. At the same time, however, the residual content of free EO or PO is reduced as set forth above.

In one particular embodiment, the teaching of the invention combines the achievement of this object with another important improvement for selective starting materials and polyalkoxylated reaction products obtainable therefrom.

In this regard, the present invention addresses the additional problem of providing alkyl polyglycol ether reaction mixtures which fully correspond in their applicational properties to the standard now demanded in practice. At the same time, however, the invention seeks to achieve a substantial improvement over comparable standard products in the low-temperature behavior of the reaction mixtures. In practice, this means that, particularly in the case of the corresponding reaction products which are capable of flowing at temperatures around room temperature or only slightly higher, the invention seeks to obtain an improved liquid characteristic and, in particular, the clear liquid state. This aspect is of particular importance for EO condensates.

In achieving this object, the invention keeps intentionally to the basic alkali metal compounds which have been successfully used as catalysts in practice. By increasing the catalyst concentration for the ethoxylation of alcohols, the invention seeks to obtain not only a reduction in the residual EO content but also an extensive improvement in the low-temperature behavior of the reaction product without, at the same time, substantially affecting its applicational properties.

The work carried out to put this principle into practice has revealed considerable difficulties in terms of process technology. The process according to the invention increases the quantity of basic alkali metal catalyst in the ethoxylation reaction to narrow the homolog distribution and, in particular, to eliminate troublesome constituents among the higher and highest ethoxylate products. However, it is necessary to this end to use the basic alkali metal catalysts in quantities which present the industrial process with considerable difficulties in terms of process technology.

Alkyl or alkyl aryl alkoxylates produced with alkaline catalysts have to be neutralized immediately after production to pH values in the range from about 6.5 to 7.5, because otherwise they undergo serious discoloration under the effect of atmospheric oxygen. Alkoxylates based on unsaturated fatty alcohols, for example oleyl alcohol, are particularly vulnerable in this regard. The neutralization of the catalyst in the reaction product is carried out with organic and/or inorganic acids, including for example gluconic acid, glycolic acid, acetic acid, formic acid, benzoic acid, lactic acid, oxalic acid, citric acid, propionic acid, phosphoric acid, methane sulfonic acid and/or diglycolic acid. Highly corrosive acids, such as sulfuric acid or hydrochloric acid, are of no practical significance.

During the neutralization reaction, the acids added react with the potassium or sodium alkoxylate present in the alkoxylate to form the corresponding salt. These salts show only limited solubility in the reaction product. If the quantity of catalyst selected for the commercial production of the alkoxylate is so high that solubility of the salts is no longer guaranteed during the neutralization reaction, first clouding and, increasingly, salt precipitation occurs in the reaction product. In practice, therefore, the quantity of catalyst hitherto used has been gauged in such a way that the salt formed with the quantity of acid required for neutralization is still just soluble in the alkoxylate reaction product. A quantity of about 0.5% by weight sodium methylate, based on the total quantity of alcohol and ethylene oxide or propylene oxide, or equivalent quantities of other basic alkali metal compounds is regarded as the limit in this respect. If the quantity of catalyst is increased beyond that limit, a salt is formed during neutralization with the acids mentioned which precipitates from the alkoxylate in the form of a viscous mass and is deposited both in the neutralization vessel (on the stirrer and the vessel walls) and in the pipes through which the alkoxylate passes to the filtration stage. Accordingly, the apparatus and pipes affected soon become so heavily contaminated on the inside that the process cycle has to be interrupted. Expensive and time-consuming cleaning measures have to be applied. The efforts involved in this regard are so considerable that the reaction products become uninteresting on economic grounds.

It has surprisingly been discovered that, if the quantity of basic alkali metal catalysts used is increased to a limited extent, not only is the residual EO content or residual PO content reduced to the required extent, but also substantial improvements can be achieved in the low-temperature stability of the end product without its applicational properties, such as washing or wetting power, emulsifying power and the like, being undesirably affected. The improvement in low-temperature behavior is of importance above all for the ethoxylates because, in general, they have a higher solidification point than corresponding propoxylates. However, the quantity of basic catalyst used in the practice of the present invention is beyond the limit of the solubility of the salt formed through neutralization in the ethoxylation product. To overcome this difficulty, the process of the invention is carried out by neutralizing the catalyst in the presence of finely divided solids which are uniformly distributed throughout the reaction mixture.

The process according to the invention thus uses such high concentrations of catalyst that, in the neutralization step, salts are precipitated as an undissolved solids phase, the neutralization step being carried out in such a way that the salt phase is precipitated in the presence of finely divided solids dispersed in the reaction product. It has surprisingly been found that incrustation inside apparatus and/or pipes can be completely prevented by this measure and that, in addition, the reaction product can be conventionally filtered without difficulty. The production of alkyl polyglycol ethers in accordance with the objective of the invention as stated above is thus possible without the loss of any advantages associated with process technology.

According to the invention, standard organic and/or inorganic filter aids are preferably used as the finely divided solids to assist crystallization. These filter aids are dispersed in the alkoxylation reaction mixture before the salt phase formed crystallizes out. In the most suitable embodiment, the filter aids are finely dispersed in the reaction product before addition of the acid is commenced.

Suitable filter aids are both inorganic materials, particularly kieselguhr, and also known organic filter aids. Organic materials may be, for example, sawdust andor/finely divided cellulose. Organic filter aids such as these are known, for example, under their tradenames or trademarks "Arbocel" and "Lignocell".

One advantage of using organic filter aids is that they can be burned together with the salt (for example sodium gluconate) obtained from the neutralization step, whereas inorganic filter aids contaminated with these salts would have to be stored at waste disposal sites.

It may be advisable in some cases to use mixtures of organic and inorganic filter aids, in which case it is particularly suitable as a rule to mix the respective constituents in a ratio of 3 : 1 to 1 : 3.

The quantity of filter aid required for salt formation is generally in the range of from 0.3 to 2% by weight, and preferably in the range of from 0.5 to 1% by weight, based on the quantity of alkoxylated product formed.

The process according to the invention can be carried out, for example, as follows:

The reaction product containing the comparatively large quantity of catalyst, which is known to have a temperature of about 150° to 180° C. on completion of the reaction, is transferred from the pressure vessel to a stirrer-equipped neutralization vessel on completion of alkoxylation. In the neutralization vessel, the reaction mixture is cooled while stirring to a temperature in the range of from 50° to 110° C. and preferably to a temperature in the range of from 80° to 100° C. and the filter aid is added to the product and homogeneously dispersed therein. Neutralization is then carried out with the selected acid. On completion of neutralization, the alkoxylate, in which the filter aid and the salt formed are homogeneously dispersed, is pumped to the filtration stage. Filtration can be carried out both in through-flow filters (filter candles, Seitz filters, etc.) and also in filter presses or rotary filters. Alkoxylates of particularly low salt content are obtained when the filtration, which is carried out in a nitrogen atmosphere, takes place at temperatures above 80° C.

Where this process of neutralization and filtration is adopted, there is no sign of any viscous and tacky salt residues either in the neutralization vessel on the walls or the stirrer or in the pipes or pumps.

In one particular embodiment of the process according to the invention, the alkoxylate reaction product is first only partially neutralized, for example to a pH value of approximately 8, by addition of acid in the neutralization vessel (with the filter aid homogeneously dispersed therein). Thereafter, the reaction product is bleached, in particular by addition of hydrogen peroxide, for example in quantities of from 0.1 to 1% by weight, based on the alkoxylate. Only after bleaching is the neutralization step completed by addition of further quantities of acid to a final pH value in the range from 6.5 to 7.5. The alkoxylate is then filtered.

The quantity of basic alkali metal compounds used as catalyst in the process according to the invention is higher than has hitherto been regarded as appropriate in practice. The quantities of catalyst used herein are above the limit of about 0.5% by weight, expressed as sodium methylate and based on the total weight of the alcohol used and ethylene oxide. Where other alkaline catalysts are used, they are used in equivalent quantities.

The particular quantity of catalyst used is co-determined by the structure of the alcohol used. Alcohols containing a sterically non-hindered hydroxyl group, i.e. in particular linear alcohols, for example of the fatty alcohol or Ziegler alcohol type, or even branched alcohols containing a sterically non-hindered primary hydroxyl group, normally require quantities of sodium methylate catalyst of from 0.5 to 1.5% by weight and preferably from 0.8 to 1.1% by weight, based on the total quantity of alcohol, ethylene oxide and/or propylene oxide used, for achieving the result in accordance with the invention of increased low-temperature stability for unchanged applicational properties.

Where sterically hindered fatty alcohols, for example such compounds as 2-hexyl-1-decanol or 2-octyl-1-dodecanol, are used, the quantity of catalyst required is normally in the range from 1.4 to 1.8% by weight sodium methylate, again based on the total quantity of alcohol, ethylene oxide and/or propylene oxide used.

By using such large quantities of catalyst and by applying the technical solution described above to remove the tacky salts inevitably formed as a result from the neutralization stage, it is possible to obtain alkoxylates which, compared with the products hitherto produced by conventional processes using smaller quantities of catalyst, show a reduced residual EO content and, at the same time, considerably better low-temperature behavior in the case of the ethoxylates or the reduced residual PO content in the case of the propoxylates without any adverse effect on, or even with improvements in, other applicationally relevant properties, such as washing power, cleaning power and emulsifying power. This improvement is particularly important with respect to the handling of nonionics of the type described herein which, in conventional production processes, are completely or partly thickened and show a tendency to form solid components, particularly on standing at room temperature. According to the invention, it is possible to improve these mixtures in their low-temperature behavior to such an extent that homolog mixtures which flow freely and, preferably, are clear at room temperature are present. Low temperature behavior may be measured in known manner by determination of the low-temperature cloud point (DIN ISO 3015), the solidification point (DIN ISO 3016) and the low-temperature clear point. In the following Examples, the low-temperature clear point was determined as follows: 100 g of the product to be tested were cooled to −40° C. so that, in every case, the sample was solid. The sample into which a thermometer had been introduced was then allowed to thaw at room temperature and the temperature at which the product just became a clear liquid was determined (low-temperature clear point).

Suitable starting materials containing an alkoxylatable alcohol function for the process according to the invention are, in particular, all those components which lend themselves to alkoxylation in the presence of limited quantities of the alkali metal catalysts, i.e. in particular starting materials which show a substantially neutral reaction. Among starting materials such as these, components of particular practical significance are those which, through the presence of sufficiently long hydrocarbon radicals, enable predetermined HLB values to be established. Starting out from components such as these, a broad range of nonionic surfactants based on linear and/or branched, saturated and/or unsaturated alcohols is available today, including for example corresponding ethoxylates of linear fatty alcohols, oxo alcohols (mixtures of linear and branched alcohols), Ziegler alcohols (linear structure), secondary alcohols from the oxidation of paraffins and comparable partial derivatives of polyhydric alcohols, such as glycerol and sorbitan partial esters with fatty acids which correspond to the alcohols discussed above. Hydrocarbon radicals containing at least 6, preferably from 8 to 36 C atoms and more preferably from 10 to 30 C atoms are of particular importance as the hydrophobic component. The carbon chain range from about $C_{10}$ to $C_{24}$ is of particular practical importance. However, the process according to the invention is also important for the production of alkylphenol alkoxylates having extremely reduced residual contents of free alkylene oxide, of which typical examples in practice are the nonylphenol ethoxylates.

In the following Examples and Comparison Examples, all the fatty alcohol ethoxylates or fatty alcohol-$EO_x$-$PO_y$-adducts are prepared as follows:

For the production of fatty alcohol ethoxylates, the quantities of fatty alcohol, ethylene oxide, and catalyst set forth in the Examples were reacted in an autoclave for about 3 to 4 hours at a temperature of 170° to 180° C. and under a pressure of 2 to at most 5 bar.

For the production of fatty alcohol-$EO_x$-$PO_y$-adducts, the quantities of fatty alcohol, ethylene oxide and catalyst set forth in the Examples are first reacted in an autoclave for about 3 to 4 hours at a temperature of 170° to 180° C. under a pressure of 2 to at most 5 bar. After the reaction had abated, as reflected in a considerable fall in the reaction pressure, the quantities of propylene oxide shown in the Examples were introduced into the autoclave and the reaction was continued for another 3 to 4 hours at 150° C. to 170° C. under a pressure of 2 to at most 5 bar.

On completion of the alkoxylation reaction, the reaction product (fatty alcohol ethoxylate or fatty alcohol-$EO_x$$PO_y$- adduct) was transferred to a stirrer-equipped neutralization vessel and 1% by weight filter aid homogeneously dispersed by stirring in the product cooled to approximately 90° C. The neutralization was then carried out with lactic acid, so that the reaction product ultimately had a pH value (1% of the product in 99% deionized water) of from 6.5 to 7.5.

The hydrophilicity (cloud point, cloud temperature, turbidimetric titration value) of the ethoxylate was determined in accordance with DIN 53 917.

The residual content of free ethylene oxide and/or propylene oxide in the reaction products described in the Examples and Comparison Examples was determined by quantitative capillary gas chromatography. The detection limit was at or below 0.1 ppm for ethylene oxide and at or below 5 ppm for propylene oxide.

The invention will be illustrated but not limited by the following examples.

EXAMPLES

Comparison Example 1

598.4 g 2-octyl-1-dodecanol, hydroxyl value 172.5, were reacted with 401.6 g ethylene oxide and 7.0 g sodium methylate (30% in methanol), corresponding to 0.2% by weight sodium methylate, based on the total quantity of alcohol and ethylene oxide. A pasty ethoxylate having the following characteristic data was obtained:

| | |
|---|---|
| OH value | 111.7 |
| % $H_2O$ | 0.08 |
| Density (70° C.) | 0.8979 g/cm$^3$ |
| Cloud temperature (5 g in 25 g 25% butyl diglycol) | 38.2° C. |
| pH value (1%) | 7.1 |
| % Polyethylene glycol | 5.5 with a molecular weight of 1600 |
| Low-temperature clear point | >50° C. |
| Solidification point | 25° C. |
| Low-temperature cloud point | 50° C. |
| Free ethylene oxide content | 90 ppm |

Example 1

596.4 g 2-octyl-1- dodecanol, hydroxyl value 172.5, were reacted with 403.6 g ethylene oxide and 60.0 g sodium methylate (30% in methanol), corresponding to 1.8% by weight sodium methylate, based on the total quantity of alcohol and ethylene oxide. An ethoxylate in the form of a clear liquid at room temperature which had the following characteristic data was obtained:

| | |
|---|---|
| OH value | 108.7 |
| % $H_2O$ | 0.08 |
| Density (70° C.) | 0.8990 g/cm$^3$ |
| Cloud temperature (5 g in 25 g 25% butyl diglycol) | 44.1° C. |
| pH value (1%) | 6.5 |
| % Polyethylene glycol | 1.2 with a molecular weight of 600 |
| Low temperature clear point | 25° C. |
| Solidification point | 8° C. |
| Low temperature cloud point | 16° C. |
| Free ethylene oxide content | <0.5 ppm |

Comparison Example 2

679.9 g oleyl alcohol, iodine value 72; hydroxyl value 212, were reacted with 520.0 g ethylene oxide and 3.6 g sodium methylate (30% in methanol), corresponding to 0.09% by weight sodium methylate, based on the total quantity of alcohol and ethylene oxide. An ethoxylate having the following characteristic data was obtained:

| | |
|---|---|
| OH value | 119.0 |
| % H$_2$O | 0.11 |
| Density (70° C.) | 0.952 g/cm$^3$ |
| Cloud temperature (5 g in 25 g 25% butyl diglycol) | 67.4° C. |
| pH value (1%) | 7.1 |
| % Polyethylene glycol | 1.2 with a molecular weight of 1000 |
| Low temperature clear point | >30° C. |
| Solidification point | 10° C. |
| Low temperature cloud point | 21° C. |
| Free ethylene oxide content | 65 ppm |

Example 2

667.3 g oleyl alcohol, iodine value 72; hydroxyl value 212, were reacted with 532.7 g ethylene oxide and 36.0 g sodium methylate (30% in methanol), corresponding to 0.9% by weight sodium methylate, based on the total quantity of alcohol and ethylene oxide. An ethoxylate having the following characteristic data was obtained:

| | |
|---|---|
| OH value | 119.8 |
| % H$_2$O | 0.06 |
| Density (70° C.) | 0.951 g/cm$^3$ |
| Cloud temperature (5 g in 25 g 25% butyl diglycol) | 67.6° C. |
| pH value (1%) | 6.8 |
| % Polyethylene glycol | 2.3 with a molecular weight of 400 |
| Low temperature clear point | 16° C. |
| Solidification point | 2° C. |
| Low temperature cloud point | 12° C. |
| Free ethylene oxide content | <0.5 ppm |

Comparison Example 3

413.0 g of a mixture of octanol/decanol, hydroxyl value 330, were reacted with 587.0 g ethylene oxide and 7.0 g sodium methylate (30% in methanol), corresponding to 0.21% by weight sodium methylate, based on the total quantity of alcohol and ethylene oxide. 9.4% of the unreacted octanol/decanol was distilled off from the ethoxylate obtained. An ethoxylate having the following characteristic data was obtained:

| | |
|---|---|
| OH value | 127 |
| % H$_2$O | 0.11 |
| Density (70° C.) | 0.954 g/cm$^3$ |
| Cloud point (1% in Water) | 58° C. |
| pH value (1%) | 7.2 |
| % Polyethylene glycol | 4.2 |
| Low-temperature clear point | >25° C. |
| Solidification point | 10° C. |
| Low-temperature cloud point | 16° C. |
| Free ethylene oxide content | 70 ppm |

Example 3

550.7 g of a mixture of octanol/decanol, hydroxyl value 330, were reacted with 849.3 g ethylene oxide and 42.0 g sodium methylate (30% in methanol), corresponding to 0.90% by weight sodium methylate, based on the total quantity of alcohols and ethylene oxide. 9.1% of the unreacted octanol/decanol was distilled off from the ethoxylate obtained. An ethoxylate having the following characteristic data was obtained:

| | |
|---|---|
| OH value | 123 |
| % H$_2$O | 0.13 |
| Density (70° C.) | 0.958 g/cm$^3$ |
| Cloud point (1% in water) | 64° C. |
| pH value (1%) | 7.1 |
| % Polyethylene glycol | 4.6 |
| Low-temperature clear point | 18° C. |
| Solidification point | 7° C. |
| Low-temperature cloud point | 10° C. |
| Free ethylene oxide content | <0.5 ppm |

Comparison Example 4

300 g of a mixture of dodecanol/tetradecanol, hydroxyl value 289, were reacted with 340 g ethylene oxide, 360 g propylene oxide and 2.9 g sodium methylate (30% in methanol), corresponding to 0.09% by weight sodium methylate, based on the total quantity of alcohol, ethylene oxide and propylene oxide. An alkoxylate having a hydroxyl value of 105 and a residual content of free propylene oxide of 3000 ppm was obtained.

Example 4

300 g of a mixture of dodecanol/tetradecanol, hydroxyl value 289, were reacted with 340 g ethylene oxide, 360 g propylene oxide and 30.0 g sodium methylate (30% in methanol), corresponding to 1.0% by weight sodium methylate, based on the total quantity of alcohol, ethylene oxide and propylene oxide. An alkoxylate having a hydroxyl value of 103 and a residual content of free propylene oxide of 2 ppm was obtained.

Comparison Example 5

300 g of a mixture of dodecanol/tetradecanol, hydroxyl value 289, were reacted with 160 g ethylene oxide, 528 g propylene oxide and 2.9 g sodium methylate (30% in methanol), corresponding to 0.09% by weight sodium methylate, based on the total quantity of alcohol, ethylene oxide and propylene oxide. An alkoxylate having a hydroxyl value of 114 and a residual content of free propylene oxide of 6000 ppm was obtained.

Example 5

300 g of a mixture of dodecanol/tetradecanol, hydroxyl value 289, were reacted with 160 g ethylene oxide, 528 g propylene oxide and 30.0 g sodium methylate (30% in methanol), corresponding to 1.0% by weight sodium methylate, based on the total quantity of alcohol, ethylene oxide and propylene oxide. An alkoxylate having a hydroxyl value of 111 and a residual content of free propylene oxide of 4 ppm was obtained.

What is claimed is:

1. A process for the preparation of alcohol polyglycol ethers consisting of the steps of
   A. reacting an alcohol having at least 6 carbon atoms with either ethylene oxide, propylene oxide, or a mixture thereof in the presence of from about 0.5% to about 1.8% by weight, expressed as sodium methylate, and based on the total weight of alcohol, ethylene oxide and propylene oxide employed in the reaction, of at least one basic alkali metal compound catalyst to produce a reaction mixture containing an alcohol polyglycol ether;

B. adding to the reaction mixture from about 0.3 to about 2% by weight, based on the weight of alcohol polyglycol ether, of at least one filter aid;

C. neutralizing the catalyst in the reaction mixture by the addition of an organic or inorganic acid thereto; and D. filtering the reaction mixture to remove therefrom the filter aid and any precipitated salts that result from step C.

2. The process of claim 1 wherein the at least one basic alkali metal compound in step A is present in at least 0.8% by weight.

3. The process of claim 1 wherein in step A the alcohol is a sterically non-hindered alcohol and the at least one basic alkali metal compound is present in from about 0.5 to about 1.5% by weight.

4. The process of claim 3 wherein the at least one basic alkali metal compound is present in from about 0.8 to about 1.1% by weight.

5. The process of claim 1 wherein in step A the alcohol is a sterically hindered alcohol and the at least one basic alkali metal compound is present in from about 1.4 to about 1.8% by weight.

6. The process of claim 1 wherein in step A the alcohol contains 8 to 36 carbon atoms.

7. The process of claim 1 wherein the alcohol contains from 10 to 30 carbon atoms.

8. The process of claim 1 wherein in step A the at least one basic alkali metal compound is at least one of a sodium alkoxylate, a potassium alkoxylate, sodium hydroxide, and potassium hydroxide.

9. The process of claim 17 wherein the at least one basic alkali metal compound is sodium methylate.

10. The process of claim 10 wherein Step A is carried out at a temperature of from about 150° C. to about 180° C.

11. The process of claim 1 wherein Step B is carried out at a temperature in the range of from about 50° C. to about 110° C.

12. The process of claim 11 wherein the temperature is in the range of about 80° C. to about 100° C.

13. The process of claim 1 wherein step D is carried out at a temperature above about 80° C.

14. The process of claim 1 wherein in Step A the at least one basic alkali metal compound is a sodium alkoxylate and is present in at least about 0.8% by weight, and the reaction is carried out at a temperature in the range of from about 150° C. to about 180° C.; step B is carried out at a temperature in the range of from about 50° C. to about 110° C.; and step D is carried out at a temperature above about 80° C.

15. The process of claim 11 wherein the alcohol polyglycol ether is a fatty alcohol-ethylene oxide-propylene oxide adduct, and step A is carried out by first reacting the fatty alcohol, ethylene oxide and catalyst, and then reacting propylene oxide with the resulting reaction product.

* * * * *

UNITED STATES PATENT AND TRADEMARK OFFICE
CERTIFICATE OF CORRECTION

PATENT NO. : 4,967,017

DATED : October 30, 1990

INVENTOR(S) : Karl Schmid et al.

It is certified that error appears in the above-identified patent and that said Letters Patent is hereby corrected as shown below:

In Claim 9, Col.12, line 3, "Claim 17" should read --Claim 8--.

In Claim 10, col. 12, line 5, "Claim 10" should read --Claim 1--.

Signed and Sealed this

Sixteenth Day of June, 1992

Attest:

DOUGLAS B. COMER

Attesting Officer

Acting Commissioner of Patents and Trademarks